United States Patent [19]
Matsukura et al.

[11] Patent Number: 6,010,701
[45] Date of Patent: Jan. 4, 2000

[54] CELL PROLIFERATOR AND APPLICATIONS THEREOF

[75] Inventors: Yumiko Matsukura; Kazuhiko Tokoro, both of Kanagawa, Japan

[73] Assignee: Takasago International Corporation, Tokyo, Japan

[21] Appl. No.: 08/947,164

[22] Filed: Oct. 8, 1997

[30] Foreign Application Priority Data

Oct. 8, 1996 [JP] Japan .................................. 8-284572

[51] Int. Cl.$^7$ .............................. A01N 65/00; C12N 5/08
[52] U.S. Cl. ......................................... 424/195.1; 435/371
[58] Field of Search ......................... 424/195.1; 435/371

[56] References Cited

U.S. PATENT DOCUMENTS 5,080,901   1/1992   Hangay et al. ...................... 424/195.1
5,149,521   9/1992   Hirsoe et al. ............................ 424/58

FOREIGN PATENT DOCUMENTS 4027227     3/1992   Germany .
359051211   3/1984   Japan .

OTHER PUBLICATIONS

Lawless, J. "The Illustrated Encyclopedia of Essential Oils," (1995) (Barnes & Noble: NY) pp. 28–30, 43–44, 50–52, 97, 106, 114, 125, 127, 136, 150, 189, 224, 228 and 233.

Gennaro, A. Ed., "Remington's Pharmaceutical Sciences" 18th edition. (1990) (Mack Publishing: Easton PA) p. 1519–1544.

Desheng, D. "Osmanthus fragrans in China," Perfumer Flavorist (1989) 14(5): 7–13 (abstract only).

*Primary Examiner*—Jean C. Witz
*Assistant Examiner*—Susan Hanley
*Attorney, Agent, or Firm*—Sughrue, Mion, Zinn, Macpeak & Seas, PLLC

[57] ABSTRACT

A cell proliferator comprising as an active ingredient a distilled residue of an extract obtained by extracting one or more specific plants as raw materials of spicery with one or more solvents selected from the group consisting of water, lower alcohols, polyol type organic solvents, petroleum ether and hexane; a spicery composition comprising the cell proliferator; an external agent for skin comprising the cell proliferator; and a bathing agent comprising the cell proliferator.

7 Claims, No Drawings

CELL PROLIFERATOR AND APPLICATIONS THEREOF

BACKGROUND OF THE INVENTION

1. Field of the Invention

The present invention relates to a cell activator and applications thereof, and particularly, to a cell activator derived from plants as raw materials of spicery.

The cell activator of the present invention comprises a distilled residue of an extract from specific spicery plants as an active ingredient, and provides an excellent cell activating function. Furthermore, the inventive cell activator is extremely safe to use.

Cell growth is promoted by using the inventive cell activator mixed with various external medicines, etc., so that cosmetic effects such as the prevention of skin aging or skin improvements and healing are expected. Specific examples include application of the cell activator of the present invention to external medicines such as lotions, creams, rinses, oils, milky lotions, shampoos, hair tonics, hair liquids, facial packs, body soaps and bathing agents. The form of these external agents is not particularly limited, and may be in the form of a liquid, powder, granules, solid, etc.

In addition to such external medicines, the cell activator of the present invention can also be blended with compositions for use in oral cavities, such as toothpaste, mouth wash, etc.

2. Description of the Related Art

Conventional cell activators include single-component activators such as hormones, vitamins, photosensitive elements, allantoin, etc., extracts derived from animals, plants and microorganisms, such as placenta extract, lactobacillus extract, sycon extract, aloe extract, carrot extract, etc. Their cell activating effects range widely from the control of keratinization such as cell growth and the promotion of differentiation to direct action on cells or indirect action by regulating the cell surroundings, such as antioxidation, anti-inflammation, healing, enlargement of capillary vessels, etc. (see *Fragrance Journal*, Vol. 22, No. 1, page 38 (1994)), Animal and plant extracts have been used in traditional medicines from ancient times, and particularly, as both Western and Eastern herb medicines in folk remedies. A large number of the active ingredients in present day medicines have been obtained from such herb medicines as a result of modern science. Even in the field of cosmetics, such ingredients are incorporated into skin-care and make-up products (see *Fragrance Journal*, Vol. 18, No. 2, page 59 (1990)). This literature discloses plants as raw materials of spicery, such as Melissa (Labiatae), Rosemary (Mannenro) (Labiatae), as well as Hop (Maraceae), etc. as plant extracts which promote metabolic action.

On the one hand, plants serving as raw materials of natural spicery compositions, which are used in the present invention, have been enjoyed not only for their aroma, but also have been used for the treatment of diseases from ancient times. The aromatic resins and plants used for treatment in old Babylonia extended to 200 or more species.

In China, the history of animal and plant extracts used as pharmaceutical preparations is extensive, and even at present, many spicery plants are incorporated into Chinese herb medicines. Furthermore, because of its anti-fungal action, "Myrrh" was well known for making mummies in Egypt.

As described above, spicery compositions and medicines have the same origin, and spicery compositions are also expected to have other physiological actions. Also disclosed are cosmetics for the prevention of skin aging obtained from the extracts of white birch and alder (birch family; Betulaceae) (see Japanese Patent Application Laid-Open No. 6-263,627), fruit passionflower (passionflower family; Passifloraceae) (see Japanese Patent Application Laid-Open No. 7-233,044), etc. Moreover, extracts from lavender plants or their cultured cells are reported to have both cell activating characteristics and excellent ultraviolet absorption characteristics (see Japanese Patent Application Laid-Open No. 64-83,013).

A cell growth test is considered particularly effective for evaluating the cell activation effect. For example, such methods include (1) the microburet method of Itzhaki and Gill where fibroblasts derived from a mouse are grown in Eagle's MEM medium containing 1% fetal bovine serum, and its protein content is determined by measuring the UV absorbance at 310 nm of a complex salt of copper and the protein (see Japanese Patent Application Laid-Open No. 64-83,013), (2) a method of determining an increase in the number of cells (see Japanese Patent Application Laid-Open No. 6-128,140), (3) a method of counting the number of human epithelial Hela cells by means of a hemocytometer (see Japanese Patent Application Laid-Open No. 6-157,280), (4) a method of counting SV40 transformed human keratinocyte and human-derived normal skin fibroblasts (CCD-45SK ATCC No. CRL1506) using the above hemocytometer (see Japanese Patent Application Laid-Open Nos. 7-215,836 and 7-233,044), and (5) a method of counting cell colonies by growing human skin cells in Dulbecco's MEM medium and fixing and staining the cells (see Japanese Patent Application Laid-Open No. 6-9366), etc.

Thereafter, a method of MTT (3-(4,5-dimethyl-2-thiazolyl-2,5-diphenyltetrazolium bromide) reduction, i.e., a cell toxicity test, has attracted attention. It was found that when incorporated into living cells, MTT undergoes reductive cleavage with NADH present in mitochondria and is thereby transformed into blue formazan. This assay indirectly indicates the metabolic activity of mitochondria, that is, the metabolic activity of cell energy. The evaluation of cell activating effect using the MTT reduction method has been reported (see *Nippon Keshohin Gijyutsusha Kaishi* (Journal of the Society of Cosmetic Chemists in Japan), vol. 27, No. 2, page 166 (1993); and Japanese Patent Application Laid-Open No. 7-285844).

However, the effects of many conventional materials or extracts having a cell-activating function are inadequate, and must therefore be blended in a large amount. Furthermore, storage stability is inadequate and these conventional materials are stimulating, such that many pose a safety problem. Moreover, even in those cases in which a single-component material is used, a problem arises in that its cost is high and a sufficient effect is not obtained.

SUMMARY OF THE INVENTION

It is therefore an object of the present invention to solve the above problems of the prior art, and to provide an agent derived from natural sources having an excellent cell activating effect.

As a result of extensive investigations, the present inventors discovered that a distilled residue from an extract of specific plants used as raw materials of spicery has a cell activating effect as determined by the MTT reduction method, to thereby achieve the present invention.

That is, as a result of their studies on the cell activating effects of natural spicery compositions, the present inventors discovered that a distilled residue of an extract obtained by extracting one or more plants selected from the group consisting of Hyacinth (*Hyacinthus orientalis*) (Liliaceae), Marigold (*Tagetes erectra* L.) (Compositae), French Marigold (*Tagetes patula* L.) (Compositae), Osmanthus (*Osmanthus fragrans*) (Oleaceae), Labdanum or Cistus (*Cistus ladaniferus* L., *Cistus cretics* L.) (Cistaceae), Vanilla (*Vanilla planifolia* Andrews or *Vanilla tahitiens* Moore) (Orchidaceae), Liatrix (*Liatris odoratissima*) (Compositae), Tonka (*Dipteryx odorata* or *Coumarouna odorata* Aubl.) (Leguminosae), Chamomile (*Matricaria chamomilla*) (Compositae), Myrrh (*Commiphora abyssinica*) (Burseraceae), Olibanum (Bosellia, *Damara Orientalis*) (Burseraceae), Coriander (*Coriandrum sativum*) (Umbelliferae) and Thyme (*Thymus vulgaris*) (Labiatae) with one or more solvents selected from the group consisting of water, lower alcohols, polyol type organic solvents, petroleum ether and hexane, provide a remarkable cell activating effect.

The present invention provides a cell activator comprising, as an active ingredient, a distilled residue of an extract obtained by extracting one or more plants selected from the group consisting of Hyacinth (*Hyacinthus orientalis*) (Liliaceae), Marigold (*Tagetes erectra* L.) (Compositae), French Marigold (*Tagetes patula* L.) (Compositae), Osmanthus (*Osmanthus fragrans*) (Oleaceae), Labdanum or Cistus (*Cistus ladaniferus* L., *Cistus cretics* L.) (Cistaceae), Vanilla (*Vanilla planifolia* Andrews or *Vanilla tahitiens* Moore) (Orchidaceae), Liatrix (*Liatris odoratissima*) (Compositae), Tonka (*Dipteryx odorata* or *Coumarouna odorata* Aubl.) (Leguminosae), Chamomile (*Matricaria chamomilla*) (Compositae), Myrrh (*Commiphora abyssinica*) (Burseraceae), Olibanum (Bosellia, *Damara Orientalis*) (Burseraceae), Coriander (*Cooriandrum sativum*) (Umbelliferae) and Thyme (*Thymus vulgaris*) (Labiatae) with one or more solvents selected from the group consisting of water, lower alcohols, polyol type organic solvents, petroleum ether and hexane.

Furthermore, the present invention provides a spicery composition having a cell activating ability comprising said cell activator, an external agent for skin comprising said cell activator, and a bathing agent comprising said cell activator.

DETAILED DESCRIPTION OF THE INVENTION

The plants used for preparing the cell activator of the present invention are the specific plants enumerated above, and these are used either singly or in combination.

Extraction from said plants is conducted using one or more solvents selected from water, lower alcohols (e.g., $C_1$ to $C_3$ alcohols) and polyol type organic solvents, petroleum ether and hexane. The lower alcohols mentioned above are preferably methanol, ethanol, etc. Examples of the polyol type organic solvents include ethylene glycol, propylene glycol, etc.

The extraction is generally carried out by immersing or gently stirring the plant in any of the above solvents at a temperature of room temperature to 50° C. The period required for the extraction is usually 30 minutes to 12 hours or thereabout.

The extracts are classified according to the extraction method used for their preparation. Generally, essential oils are obtained by squeezing fruits and pericarp, or by distilling flowers, leaves, stems, etc. with water vapor. The term "absolute" refers to an extract prepared by extracting a concrete mainly from flowers by a variety of methods, and then further extracting with alcohol and concentrating the same to thereby remove wax components, proteins, pigments, etc. The term "resinoid" refers to an extract prepared by concentrating extracts from roots, stems and lichen or from resinous secretions (other than flowers, fruits, etc.). Usually, resinoid extracts are semi-solid and contain soluble resins.

The extract is then distilled. The distillation is carried out under reduced pressure, usually at 1 to 200 mmHg, preferably 1 to 20 mmHg, until all effluent components are removed by distillation at a temperature of 40 to 95° C. The time period required for the distillation is generally in the range of 30 minutes to two hours or thereabout. The distillation can be carried out using well known distillation techniques, or using a simple still equipped with a Claisen unit.

The resulting distilled residue is removed as such or after dissolving and diluting the distilled residue with alcohols such as ethanol, propylene glycol, etc. In the present invention, the distilled residue of the extract is preferably diluted with any of the solvents enumerated above for ease in handling, and at the same concentration as that of the original extract. However, the odor of the distilled residue or distilled residue reconstituted with a solvent is quite different from that of the original extract, and the respective compositions are therefore also different.

The effective amount of the cell activator of the present invention is appropriately determined depending on the intended application. For example, the amount of the distilled residue that is reconstituted with a solvent, preferably at about the same concentration as that of the original extract, is generally incorporated in an amount of 0.1 to 50% by weight, preferably 0.1 to 20% by weight in a spicery composition. For mixing with cosmetics, milky lotion, cream, etc., the addition amount is usually 0.1 to 5% by weight, preferably 0.1 to 2% by weight. Furthermore, for body soap or bathing agents, the addition amount is generally 0.1 to 10% by weight, preferably 1 to 5% by weight.

The cell activator is mixed by diluting with a single solvent or a mixture of organic solvents such as a polyol or a lower alcohol conventionally used in spicery. A mixture of the cell activator in a solvent containing a surface active agent can also be used. Furthermore, the cell activator can be mixed with conventional spicery materials.

EXAMPLES

Hereinafter, the present invention is described in more detail by the following Examples which, however, are not intended to limit the scope of the invention.

Example 1

Production of Various Extracts

Flowers of fragrant olive (a plant of the genus Osmanthus of the Oleaceae family) were extracted with petroleum ether or hexane and filtered to remove the flowers, and the solvent was then removed under reduced pressure to obtain a concrete. The resulting concrete was extracted under heating with a 10-fold excess of ethanol and left standing at room temperature overnight. Thereafter, the filtrate was kept at 4° C. to remove precipitates, and the supernatant was concentrated under reduced pressure to provide a 20% absolute of the concrete (Osmanthus extract).

For other extracts, e.g., in the case of labdanum, leaves and small branches of labdanum were extracted with hot water to obtain labdanum gum which was then extracted with benzene to provide a resinoid. Cistus oil was obtained by distilling the labdanum gum with water vapor. Chamomile oil as used herein was obtained by harvesting flowers, and drying and distilling the same with water vapor.

Furthermore, the following extracts whose production methods were confirmed were used in the following Examples and Comparative Examples.

(1) Examples

Hyacinth Absolute (a product of COMPAGNIE D ARGEVILLE S. A. Co., Ltd.)

Marigold Absolute (a product of CAMILLI ALBERT & LALOUS)
   Cistus Oil (JAPAN SANOPHA Co., Ltd.)
   Labdanum Resinoid (PIERRE CHAUVET Co., Ltd.)
   Vanilla Absolute (QUEST Co., Ltd.)
   Vanilla Resinoid (ARCO (CHARABOT) ETABLISSEMENTS ARCO Co., Ltd.)
   Cistus Absolute (GIVAUDAN Co., Ltd.)
   Liatrix Absolute (ARCO (CHARABOT) ETABLISSEMENTS ARCO Co., Ltd.)
   Tonka Resinoid (V. MANE FILS Co., Ltd.)
   Chamomile Blue (ARCO (CHARABOT) ETABLISSEMENTS ARCO Co., Ltd.)
   Myrrh Resinoid (GAMILLI ALBERT & LALOUS Co., Ltd.)
   Olibanum Resinoid (PIERRE CHAUVET Co., Ltd.)
   Coriander Absolute (PIERRE CHAUVET Co., Ltd.)
   Thymus Morocco Absolute (JAPAN SANOPHA Co., Ltd.)

(2) Comparative Examples

Mimosa Absolute (LABOROTOIRE MINIQUE REMY Co., Ltd.)
   Benzoin Absolute (PIEERRE CHAUVET Co., Ltd.)
   Violet Absolute (CAMILLI ALBERT & LALOUS Co., Ltd.)
   Oakmoth Absolute (ARCO (CHARABOT) ETABLISSEMENTS ARCO Co., Ltd.)
   Rosemary Absolute (ARCO (CHARABOT) ETABLISSEMENTS ARCO Co., Ltd.)

Distillation Method

A still was charged with 9 g of Hyacinth Absolute which is one of the above extracts and heated under reduced pressure at 10 mmHg in a water bath at 90° C. The sample was distilled for 2 hours. The resulting distillate was 5 g and the residue was 4 g. Other extracts were treated in the same manner to obtain a residue of each extract. The content (%) of the remaining residue (weight of the distilled residue divided by the weight of the extract prior to distillation) varies depending on the manner of distillation and the type of plant extract, and was 74% for Marigold Absolute and 14% for Cistus Absolute.

Example 2

Cell Activation Test by the MTT Method

MTT (3-(4,5-dimethyl-2-thiazolyl)-2,5-diphenyltetrazolium bromide) is a water-soluble yellow pigment which undergoes reductive cleavage by an enzyme (NADH) in mitochondria to form water-insoluble blue formazan when incorporated into living cells. Because it is known that the amount of formazan thus formed is in good agreement with the amount of NADH present, the metabolic activity of the cells can be quantitatively determined in an indirect manner by solubilizing the formazan and measuring its absorbance.

This method is widely used to measure cell toxicity. In this method, a cell activation test was carried out. The detailed procedures are as follows:

Normal human fetal lung fibroblast (WI-38) was inoculated in an amount of $5'10^4$ cells/ml into Dulbecco's modified Eagle MEM medium (Nissui Seiyaku K. K.) containing 1% fetal bovine serum. This medium was then placed in a 96-well microtiter plate in an amount of 200 µl/well and cultured in a $CO_2$ incubator (5% $CO_2$, 37° C.). The cells adhered to the bottom of each well 2 to 3 hours thereafter.

Twenty-four hours later, the medium in each well was removed, and the medium containing 2 to 500 ppm of the sample by a 2-fold serial dilution with ethanol as a solvent was added to each well. The cells were then cultured in the presence of the sample for 48 hours. Thereafter, the medium was removed again, and 180 µl of MEM medium not containing the sample was added thereto. Then, MTT (Nakarai Tesque), dissolved in an amount of 8 mg/ml in phosphate buffered saline (PBS (−)) and sterilized by filtration through a membrane, was added to each well in an amount of 20 µl per well. The medium was removed after culturing for 2.5 hours. The MTT formazan thus formed was dissolved by adding isopropanol (200 µl per well), and its absorbance was determined at 595 nm with a reference at 655 nm in a microplate reader (BIO-RAD).

A well containing only ethanol was used as a control, and wells having a higher absorbance than the control were evaluated as having cell-activating activity. In the above procedure, the cell activating effect was determined using the sample after it was adjusted to the same concentration as that of the residue in the original extract by diluting the distilled residue of the extract with ethanol. It was confirmed that the effluent components obtained upon distillation did not exhibit the cell activating property of the present method, and that the residue had a similar or stronger cell activator property as compared to that of the extract prior to distillation. The results are shown in Table 1. The results of the distilled residues from Violet Absolute, Oakmoth Absolute and Rosemary Absolute are shown as Comparative Examples in the same table.

| Composition of phosphate buffered saline PBS (−) | |
| --- | --- |
| NaCl | 0.8% |
| KCl | 0.02% |
| $Na_2HPO_4.12H_2O$ | 0.29% |
| $KH_2PO_4$ | 0.02% |

TABLE 1

(Effective Concentration for Cell Activating Action (ppm))

| | |
| --- | --- |
| Hyacinth Absolute | 8, 16, 31 |
| Marigold Absolute | 62, 125, 250 |
| Osmanthus Absolute | 31, 62, 125 |
| Cistus Oil | 16, 31, 62, 125 |
| Labdanum Resinoid | 31, 62 |
| Vanilla Absolute | 16, 31 |
| Vanilla Resinoid | 8, 16, 31 |
| Cistus Absolute | 8, 16, 31 |

TABLE 1-continued (Effective Concentration for Cell Activating Action (ppm))

| | |
|---|---|
| Liatrix Absolute | 16, 31 |
| Tonka resinoid | 62, 125 |
| Chamomile Blue | 31, 62 |
| Myrrh Resinoid | 16, 31, 62 |
| Olibanum Resinoid | 16, 31, 62 |
| Coriander Absolute | 31, 62, 125 |
| Thymus Morocco Absolute | 8, 16, 31 |
| No sample addition | not effective at 2 to 500 ppm |
| Violet Absolute | not effective at 2 to 500 ppm |
| Oakmoth Absolute | not effective at 2 to 500 ppm |
| Rosemary Absolute | not effective at 2 to 500 ppm |

Example 3

Cell Growth Test

Human-derived normal skin fibroblast (NB1RGB) was inoculated in an amount of $2 \times 10^4$ cells/ml into Dulbeccols modified Eagle MEM medium (Nissui Seiyaku K. K.) containing 10 % fetal bovine serum. This medium was then introduced into bottles having a bottom surface area of 25 cm$^2$ (Iwaki Glass K. K.) in an amount of 5 ml per bottle and cultured in a $CO_2$ incubator (5% $CO_2$, 37° C.) for 24 hours.

Then, the medium was exchanged. The old medium was sucked off and fresh medium (5 ml) was added to the bottle. After changing the medium, an appropriate amount of sample was dissolved in an 0.2% ethanol solution to give the final concentration shown in Table 2. As a control, only ethanol (0.2% ) was added. After adding the samples or ethanol, the bottles were cultured for an additional one week. In this case, the media containing samples or ethanol were again exchanged three days after the first medium exchange. After culturing for one week, the cells were peeled off from each bottle with trypsin (DIFCO), and the number of cells in each bottle was determined with a Coulter Counter (Sysmex). Following the same procedure, cells were simultaneously cultured in medium containing only ethanol, as a control, and the number of cells were determined.

The number of cells after culturing in a bottle containing the sample solution was determined relative to the number of the cells in the control taken as 100. The results are shown in Table 2. As for the Comparative Examples, the results obtained using the distilled residues from Mimosa Absolute and Benzoin Absolute are also shown in the same table. The cell growth promoting action was determined using the sample after it was adjusted to the same concentration as that of the residue in the original extract by diluting the distilled residue of the extract with ethanol. It was confirmed that the effluent components upon distillation did not exhibit the cell activating property of the present method, and that the residue had a similar or stronger cell activating property as compared to that of the extract prior to distillation.

As seen from Table 2, the distilled residues of the plant extracts of the present invention significantly promoted the growth of cells, and therefore have a cell activating effect.

TABLE 2

(Cell Growth promoting Action)

| | Samples | Test Concentration (ppm) | Cell Activation (%) |
|---|---|---|---|
| Example | Hyacinth Absolute | 16 | 120 |
| | Marigold Absolute | 62 | 140 |
| | Osmanthus Absolute | 62 | 110 |
| | Cistus Oil | 31 | 120 |
| | Labdanum resinoid | 16 | 120 |
| | Vanilla Absolute | 31 | 120 |
| | Vanilla Resinoid | 8 | 120 |
| | Cistus Absolute | 4 | 135 |
| | Liatrix Absolute | 4 | 115 |
| | Tonka Resinoid | 31 | 120 |
| | Chamomile Blue | 8 | 115 |
| | Myrrh Resinoid | 8 | 110 |
| | Olibanum Resinoid | 16 | 110 |
| | Coriander Absolute | 8 | 110 |
| | Thymus Morocco Absolute | 8 | 135 |
| | No sample addition | 0 | 100 |
| Comparative Example | Mimosa Absolute | 31, 62, 125 | 100 |
| | Benzoin Absolute | 8, 16, 31 | 100 |

Example 4

The distilled residues of the plant extracts according to the present invention were used in the following formulae to prepare spicery compositions.

| | weight-g |
|---|---|
| (1) White Rose-like spicery composition | |
| hydroxy citronellal | 0.25 |
| α-amylcinnamic aldehyde | 0.50 |
| galaxolide (1,3,4,6,7,8-Hexahydro-4,6,6,7,8,8-hexamethylcyclopenta-γ-2-benzopyran, product of International Flavor and Fragrance) | 2.00 |
| benzyl acetate | 0.75 |
| citronallol 950 | 11.5 |
| δ-damascon | 0.125 |
| dimethyl benzyl carbinyl acetate | 0.125 |
| 95% ethanol | 1.235 |
| geraniol pure | 12.5 |
| geranyl acetate | 0.25 |
| ionone SP | 1.50 |
| l-rose oxide | 0.05 |
| 3,7-dimethyl-2,6-octadienal | 0.05 |
| linalool | 1.00 |
| linalyl acetate | 0.25 |
| methyl eugenol | 0.15 |
| 100% musk ketone | 1.00 |
| ethylene brassylate 93 | 2.00 |
| rose oil ADJ MM-1942 | 3.75 |
| phenyl ethyl alcohol | 5.00 |
| triethyl citrate | 3.89 |
| musc tincture | 1.50 |
| Ylang Ylang Bourbon | 0.50 |
| diluent for vanilla distilled residue | 50.0 |
| (2) Muguet-like spicery composition | |
| acetophenone | 0.05 |
| benzoic acid | 22.225 |
| citronellol 950 | 1.40 |
| acetate citronelyl | 0.125 |
| cyclamen aldehyde EX | 1.40 |
| geraniol pure | 2.40 |
| geranyl acetate | 0.20 |
| methyl dihydro jasmonate | 0.10 |
| hexyl cinnamic aldehyde SP | 5.40 |
| hydrotropic aldehyde | 0.05 |
| indole pure | 1.50 |

|  | weight-g |
|---|---|
| jasmine VF-8231 | 0.25 |
| 1,3-nonanedienyl acetate | 0.10 |
| 9-decenol | 5.25 |
| jasmine lactone #411 | 0.10 |
| linalool | 0.50 |
| nerol pure | 0.15 |
| neryl acetate | 0.50 |
| phenyl ethyl salicylate | 2.10 |
| phenyl ethyl alcohol | 5.20 |
| triethyl citrate | 1.00 |
| diluent for distilled residue of Cistus Absolute (ethanol) | 50.0 |

Example 5

The distillation residues of the plant extracts of the present invention were used to prepare an external medicine for skin and a bath agent in the following formulae.

|  | weight-% |
|---|---|
| (1) Cosmetic water | |
| conc. glycerin | 3.0 |
| 1,3-butylene glycol | 2.0 |
| polyoxyethylene sorbitan monolaurate | 1.0 |
| ethanol | 5.0 |
| Muguet-like spicery composition of Example 4 | trace amount |
| preservative (methylparaben) | suitable amount |
| purified water | adjusted to 100% |
| (2) Milky lotion | |
| squalane | 5.0 |
| vaseline | 2.0 |
| bees wax | 0.5 |
| sorbitan sesquioleate | 0.8 |
| polyoxyethylene oleyl ether (20.E.0) | 1.2 |
| Muguet-like spicery composition of Example 4 | 0.5 |
| preservative (methylparaben) | suitable amount |
| humectant (propylene glycol) | 5.0 |
| ethanol | 5.0 |
| viscous material (carboxyvinyl polymer, 1.0% aqueous solution) | 20.0 |
| alkali (potassium hydroxide) | 0.1 |
| purified water | adjusted to 100% |
| (3) Cream | |
| stearic acid | 2.0 |
| stearyl alcohol | 7.0 |
| hydrogenated lanolin | 2.0 |
| squalane | 5.0 |
| 2-octyl dodecanol | 6.0 |
| polyoxyethylene cetyl ether (25E.O) | 3.0 |
| lipophilic glycerin monostearate | 2.0 |
| White Rose-like spicery composition of Example 4 | 0.3 |
| preservative (anti-oxidant) | suitable amount |
| propylene glycol | 5.0 |
| purified water | adjusted to 100% |
| (4) Facial pack | |
| polyvinyl alcohol | 15.0 |
| sodium carboxymethyl cellulose | 5.0 |
| propylene glycol | 3.0 |
| ethanol | 10.0 |
| White Rose-like spicery composition of Example 4 | 0.5 |
| preservative (methylparaben) and anti-oxidant BHT (butylated hydroxytoluene, 2,6-di-tert-butyl-p-cresol) | suitable amount |
| purified water | adjusted to 100% |
| (5) Body soap | |
| tetrasodium edetate | 0.2 |
| triethanolamine | 11.4 |
| coconut fatty acid | 15.6 |
| ethylene glycol distearate | 1.0 |
| 2-alkyl-N-carboxymethyl-N-hydroxy-ethylimidazolium betaine (35%) | 10.0 |
| coconut fatty acid diethanolamide | 3.0 |
| propylene glycol | 3.0 |
| preservative (butylparaben) | suitable amount |
| coloring agent | suitable amount |
| Muguet-like spicery composition of Example 4 | 0.5 |
| purified water | adjusted to 100% |
| (6) Shampoo | |
| sodium alkyl ether sulfate | 16 |
| diethanolamide laurate | 4 |
| propylene glycol | 2 |
| preservative (methylparaben) | trace amount |
| pigment | trace amount |
| White Rose-like spicery composition of Example 4 | trace amount |
| purified water | adjusted to 100% |
| (7) Cream rinse | |
| stearyl trimethyl ammonium chloride | 1.5 |
| cetanol | 2.0 |
| 2-octyldodecanol | 1.0 |
| cationic cellulose | 0.5 |
| polyoxyethylene cetyl ether | 1.0 |
| propylene glycol | 5.0 |
| methylparaben | 0.1 |
| White Rose-like spicery composition of Example 4 | 0.2 |
| purified water | adjusted to 100% |
| (8) Bath salt (granule type) | |
| sodium sulfate | 45 |
| sodium bicarbonate | 52 |
| sodium borate | 2 |
| sodium carboxymethyl cellulose | 1 |
| pigment | suitable amount |
| Muguet-like spicery composition of Example 4 | suitable amount |
| (9) Cream foundation | |
| stearic acid | 5.0 |
| lipophilic glyceryl monostearate | 2.5 |
| cetostearyl alcohol | 1.0 |
| propylene glycol monolaurate | 3.0 |
| fluid paraffin | 7.0 |
| isopropyl myristate | 8.0 |
| butylparaben | suitable amount |
| triethanolamine | 1.2 |
| sorbitol | 3.0 |
| methylparaben | suitable amount |
| titanium dioxide | 8.0 |
| kaolin | 5.0 |
| talc | 2.0 |
| bentonite | 1.0 |
| coloring pigment | suitable amount |
| White Rose-like spicery composition of Example 4 | suitable amount |
| purified water | adjusted to 100% |

Example 6

In this example, the cell activating effect of the spicery compositions prepared in Example 4 were evaluated by the MTT method. The results are shown below.

|  | effective concentration (ppm) |
| --- | --- |
| White Rose-like spicery composition | 8, 16, 31 |
| Muguet-like spicery composition | 8, 16, 31 |

As described above, the distilled residue of the extract of specific plants used as a natural raw material of spicery was found to have a cell activating function, and the present invention provides a cell activator containing this residue as an active ingredient. The cell activator prevents and improves liver spots and wrinkles caused by aging. Furthermore, this activator can be incorporated into basic cosmetics such as creams, lotions, milky lotions, facial packs, etc., make-up cosmetics such as foundation, lip stick, etc., hair cosmetics such as hair cream, hair lotion, hair tonic, shampoo, rinse, etc., bathing agents, soap and body soap, as well as oral preparations such as toothpaste, mouth wash, etc.

While the invention has been described in detail and with reference to specific embodiments thereof, it will be apparent to one skilled in the art that various changes and modifications can be made therein without departing from the spirit and scope thereof.

What is claimed is:

1. A method for promoting proliferation of skin cells comprising contacting a cell whose growth is to be proliferated with a cell growth proliferator, said cell growth proliferator being a distilled residue of an extract obtained by distilling said extract from at least one plant under reduced pressure, said at least one plant being selected from the group consisting of Hyacinth (*Hyacinthus orientalis*) (Liacele), Marigold (*Tagetes erectra* L.) (Compositae), Labdanum (*Cistus ladaniferus* L., *Cistus cretics* L.) (Cistaceae), Vanilla (*Vanilla planifolia* Andrews or *Vanilla tahitiens* Moore) (Orchidaceae), Tonka (*Dipteryx odorata* or *Coumarouna odorata* Aubi.) (Legosae), and Thyme (*Thyinus vulgaris*) (Labiatae) wherein said method results in at least 120% activation of said population containing said cell.

2. The method according to claim 1, comprising reconstituting said distilled residue with a solvent to about the same concentration as that of the extract prior to distillation before contacting said cell with said residue.

3. The method according to claim 1, comprising removing effluent components from said extract at a distillation temperature of 40° C. to 95° C.

4. The method according to claim wherein said contacting comprises applying said cell growth proliferator to the skin.

5. The method according to claim 4, wherein the cell growth proliferator is applied to the skin in a composition, said cell growth proliferator being present in said composition in an amount of 0.1 to 5 percent by weight.

6. The method according to claim 1, wherein the plant is selected from the group consisting of Marigold (*Tagetes erectra* L.) (Compositae), Labdanum (*Cistus ladaniferus* L., *Cistus cretics* L.) (Cistaceae), and Thyme (*Thymus vulgaris*) (Labiatae) and said cell activation is at least 130%.

7. The method according to claim 1, wherein the plant is selected from the group consisting of Tonka (*Dipteryx odorata* or *Coumarouna odorata* Aubl.) (Leguminosae) and Vanilla (*Vanilla planifolia* Andrews or *Vanilla tahitiens* Moore) (Orchidaceae).

* * * * *